United States Patent
Havens et al.

(10) Patent No.: US 11,114,617 B2
(45) Date of Patent: Sep. 7, 2021

(54) SPIROACRIDINE DERIVATIVES

(71) Applicants: Dow Global Technologies LLC, Midland, MI (US); Rohm and Haas Electronic Materials LLC, Marlborough, MA (US)

(72) Inventors: Laura Havens, Midland, MI (US); Sukrit Mukhopadhyay, Midland, MI (US); David S. Laitar, Midland, MI (US); David D. Devore, Midland, MI (US); Aaron A. Rachford, South Grafton, MA (US); Erich J. Molitor, Midland, MI (US)

(73) Assignees: Rohm and Haas Electronic Materials LLC, Marlborough, MA (US); Dow Global Technologies LLC, Midland, MI (US)

( * ) Notice: Subject to any disclaimer, the term of this patent is extended or adjusted under 35 U.S.C. 154(b) by 311 days.

(21) Appl. No.: 16/320,273

(22) PCT Filed: Aug. 11, 2017

(86) PCT No.: PCT/US2017/046504
§ 371 (c)(1),
(2) Date: Jan. 24, 2019

(87) PCT Pub. No.: WO2018/038938
PCT Pub. Date: Mar. 1, 2018

(65) Prior Publication Data
US 2021/0020837 A1    Jan. 21, 2021

Related U.S. Application Data

(60) Provisional application No. 62/379,909, filed on Aug. 26, 2016.

(51) Int. Cl.
*H01L 51/00* (2006.01)
*C07D 471/04* (2006.01)
*C07F 7/10* (2006.01)

(52) U.S. Cl.
CPC ........... *H01L 51/00* (2013.01); *C07D 471/04* (2013.01); *C07F 7/10* (2013.01)

(58) Field of Classification Search
CPC .. C07D 498/06; C07D 498/10; C07D 498/16; C07D 498/20; H01L 51/0072
See application file for complete search history.

(56) References Cited

U.S. PATENT DOCUMENTS 10,886,476 B2 * 1/2021 Fuchiwaki ........... C07D 471/04

* cited by examiner

*Primary Examiner* — Noble E Jarrell
(74) *Attorney, Agent, or Firm* — G. Creston Campbell

(57) ABSTRACT

Provided is a composition comprising a compound having structure (I) wherein each of $A^1, A^2, A^3, A^4, A^5, A^6, A^7$, and $A^8$ is independently $CR^{12}$ or N; wherein one to four of $A^1, A^2, A^3, A^4, A^5, A^6, A^7$, and $A^8$ are N; wherein $J^1$ is C or Si; wherein $J^2$ is $C(R^{13})_n$, O, $(C(R^{13})_n)_2$, S, $NR^{13}$, or Se; wherein n is 1 or 2; wherein each of $R^1, R^2, R^3, R^4, R^5, R^6, R^7, R^8, R^9, R^{10}, R^{11}, R^{12}$, and $R^{13}$ is independently H, deuterium, or an organic group. Also provided is a method of making the composition, a method of making an organic light-emitting diode using the composition, and an organic light-emitting diode made by that method.

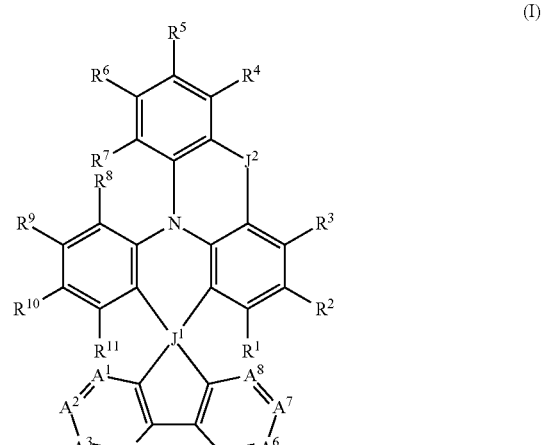

6 Claims, 1 Drawing Sheet

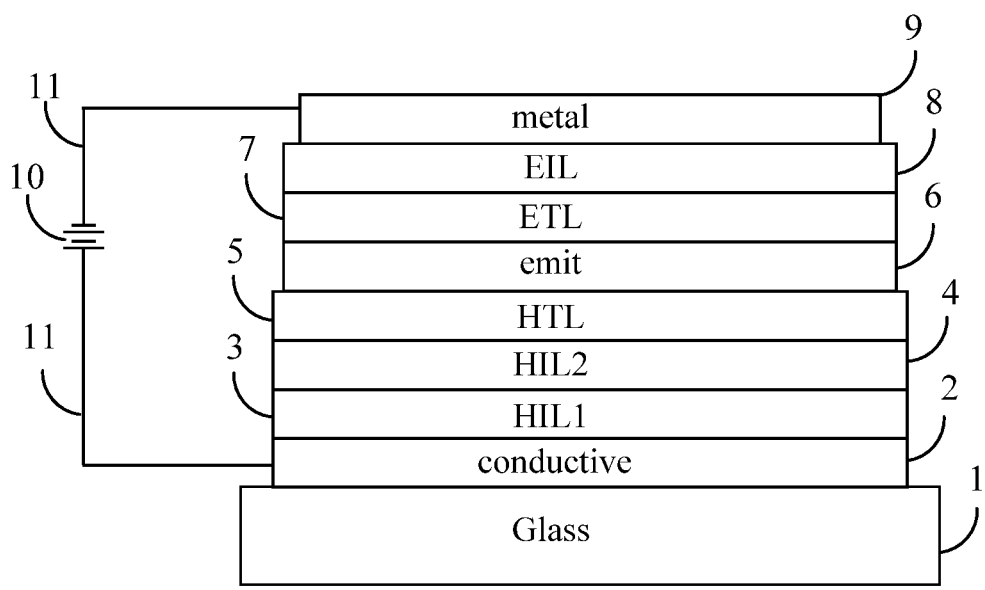

SPIROACRIDINE DERIVATIVES

An important class of electronic devices are light-emitting diodes (LEDs). A useful type of LED employs one or more organic compounds as the emissive material (OLEDs). Prior to the present invention, typical emissive materials were either iridium complexes or fluorescent organic molecules. Each of these classes of emissive materials has at least one drawback: Iridium complexes are expensive, and the fluorescent molecules used heretofore have been inefficient at converting current into emitted light. Also, fluorescent molecules that were used heretofore had typically had undesirably broad emission spectra. It is also desirable that the emissive material emits with an emission spectrum having a peak wavelength of between 400 nm and 500 nm. It is additionally desirable that the emissive material have a photoluminescence quantum yield as near to 100% as possible.

KR020208 describes acridine derivatives used as electroluminescent compounds. It is desired to provide electroluminescent compounds that have one or more of the following benefits: less expensive than electroluminescent iridium complexes; efficient conversion of current into emitted light; and a desirably narrow emission spectrum.

The following is a statement of the invention.

A first aspect of the present invention is a composition comprising a compound having structure (I)

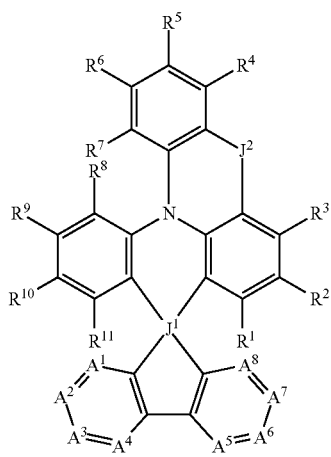

(I)

wherein each of $A^1$, $A^2$, $A^3$, $A^4$, $A^5$, $A^6$, $A^7$, and $A^8$ is independently $CR^{12}$ or N; wherein one to four of $A^1$, $A^2$, $A^3$, $A^4$, $A^5$, $A^6$, $A^7$, and $A^8$ are N; wherein $J^1$ is C or Si; wherein $J^2$ is $C(R^{13})_n$, O, $(C(R^{13})_n)_2$, S, $NR^{13}$, or Se; wherein n is 1 or 2; wherein each of $R^1$, $R^2$, $R^3$, $R^4$, $R^5$, $R^6$, $R^7$, $R^8$, $R^9$, $R^{10}$, $R^{11}$, $R^{12}$, and $R^{13}$ is independently H, deuterium, or an organic group.

A second aspect of the present invention is a method of making the composition of the first aspect, comprising making a mixture of a compound having structure II, a base having pKa of the conjugate acid of 8 or higher, and a compound $G_iX$, wherein structure II is

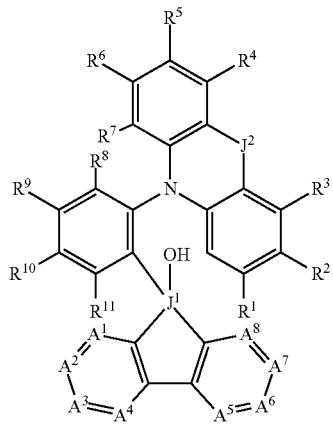

(II)

wherein $J^1$, $J^2$, $A^1$, $A^2$, $A^3$, $A^4$, $A^5$, $A^6$, $A^7$, $A^8$, $R^1$, $R^2$, $R^3$, $R^4$, $R^5$, $R^6$, $R^7$, $R^8$, $R^9$, $R^{10}$, $R^{11}$, $R^{12}$, and $R^{13}$ are the same as in claim 1, wherein G is selected from the group consisting of methanesulfonyl, trifluoromethanesulfonyl, and 4-methylbenzenesulfonyl; wherein X is a halogen or O; with the proviso that if X is a halogen, then i is 1, and if X is O, then i is 2.

A third aspect of the present invention is a method of making an organic light-emitting diode comprising the step of forming a layer on a substrate, wherein the layer comprises the composition of the first aspect.

A fourth aspect of the present invention is an organic light-emitting diode comprising the composition of the first aspect.

The following is a brief description of the drawing.

FIG. 1 shows one embodiment of an OLED made using a composition of the present invention.

The following is a detailed description of the invention.

As used herein, the following terms have the designated definitions, unless the context clearly indicates otherwise.

The term "alkoxy," as described herein, refers to an alkyl in which at least one hydrogen atom is substituted with an oxygen atom, O.

The term "alkyl," as described herein, refers to an organic radical derived from an alkyl hydrocarbon by deleting one hydrogen atom therefrom. An alkyl group may be a linear, branched, cyclic or a combination thereof. The term "substituted alkyl," as used herein, refers to an alkyl, in which at least one hydrogen atom is substituted with a substituent that comprises at least one heteroatom. Heteroatoms include, but are not limited to, O, N, P and S. Substituents include, but are not limited to, halide, OR', $NR'_2$, $PR'_2$, $P(=O)R'_2$, $SiR'_3$; where each R' is independently a $C_1$-$C_2$ hydrocarbyl group.

The "anode" is the electrode by which the holes enter into the device (item 1 in FIG. 1). The anode is disposed on a substrate. The anode is typically made from a metal, a metal oxide, a metal halide, an electroconductive polymer, or combinations thereof.

The term "aryl," as described herein, refers to an organic radical derived from aromatic hydrocarbon by deleting one hydrogen atom therefrom. An aryl group may be a monocyclic and/or fused ring system, each ring of which suitably contains from 5 to 7, preferably from 5 or 6 atoms. Structures wherein two or more aryl groups are combined through single bond(s) are also included. Specific examples include, but are not limited to, phenyl, tolyl, naphthyl, biphenyl, anthryl, indenyl, fluorenyl, benzofluorenyl, phenanthryl, triphenylenyl, pyrenyl, perylenyl, chrysenyl, naphtacenyl, fluoranthenyl and the like. The naphthyl may be 1-naphthyl or 2-naphthyl, the anthryl may be 1-anthryl, 2-anthryl or 9-anthryl, and the fluorenyl may be any one of 1-fluorenyl, 2-fluorenyl, 3-fluorenyl, 4-fluorenyl and 9-fluorenyl. The term "substituted aryl," as used herein, refers to an aryl, in which at least one hydrogen atom is substituted with a substituent comprising at least one heteroatom, and any combination thereof. Heteroatoms include, but are not limited to, O, N, P and S. Substituents include, but are not limited to, halide, OR', NR'$_2$, PR'$_2$, P(=O)R'$_2$, SiR'$_3$; where each R' is independently a $C_1$-$C_{20}$ hydrocarbyl group.

The term "aryloxy," as described herein, refers to an aryl in which at least one hydrogen atom is replaced with an oxygen atom, O.

The term "amine" as described herein refers to a compound having one or more amine nitrogen atoms. An amine nitrogen atom is a nitrogen atom that is part of a structure $R^{41}NH_2$, $R^{41}R^{42}NH$, or $R^{41}R^{42}R^{43}N$, where each of $R^{41}$, $R^{42}$, and $R^{43}$ is a substituted or unsubstituted alkyl or aryl group. $R^{41}$, $R^{42}$, and $R^{43}$ may be separate groups, or any two or more of $R^{41}$, $R^{42}$, and $R^{43}$ may be connected to each other to form one or more aromatic ring or one or more aliphatic ring or a combination thereof. An amine may have exactly one amine nitrogen atom or may have two or more amine nitrogen atoms. An amine having one or more aromatic rings is an aromatic amine.

The "cathode" is the electrode through which the electrons enter into the device (item 9 in FIG. 1). The cathode is typically made from a metal, a metal oxide, a metal halide, an electroconductive polymer, or a combination thereof.

"Dopant" and like terms, refer to a material that undergoes radiative emission from an excited state. The excited state can be generated, for example, by application of electrical current in an electroluminescent device or by energy transfer from the excited state of another molecule.

"Electron injection layer," or "EIL," and like terms is a layer for efficiently injecting electrons injected from the cathode into the electron transport layer.

"Electron transport layer," or "ETL," and like terms is a layer disposed between the emitting layer and the electron injection layer for improving the luminescent efficiency of the OLED. When placed in an electric field, the electron transport layer transports electrons injected from the cathode toward the emitting layer. The material or composition of the ETL typically has a high electron mobility for efficiently transporting injected electrons.

"Electron Volt" or "eV" is the amount of energy gained (or lost) by the charge of a single electron moved across an electric potential difference of one volt.

"Emitting layer" and like terms, is a layer located between electrodes (anode and cathode) and when placed in an electric field is excited by the recombination of holes injected from the anode through the hole injection layer with electrons injected from the cathode through the electron transport layer, the emitting layer being the primary light-emitting source. The emitting layer consists of host and dopant. The host material could be bipolar or unipolar, and may be used alone or by combination of two or more host materials. The opto-electrical properties of the host material may differ to which type of dopant (Phosphorescent or Fluorescent) is used. For phosphorescent dopants, the assisting host materials should have high triplet energies to confine triplets of the dopant.

The term "heteroalkyl," as described herein, refers to an alkyl group, in which at least one carbon atom or CH group or $CH_2$ is substituted with a heteroatom or a chemical group containing at least one heteroatom. Heteroatoms include, but are not limited to, O, N, P and S. A heteroalkyl group may be a linear, branched, cyclic or a combination thereof. The term "substituted heteroalkyl," as used herein, refers to an heteroalkyl, in which at least one hydrogen atom is substituted with a substituent that comprises at least one heteroatom. Heteroatoms include, but are not limited to, O, N, P and S. Substituents include, but are not limited to, halide, OR", NR"$_2$, PR"$_2$, P(=O)R"$_2$, SiR"$_3$; where each R" is independently a $C_1$-$C_{20}$ hydrocarbyl group.

The term "heteroaryl," as described herein, refers to an aryl group, in which at least one carbon atom or CH group or $CH_2$ of an aromatic ring is replaced with a heteroatom or a chemical group containing at least one heteroatom. Heteroatoms include, but are not limited to, O, N, P and S. The heteroaryl may be a 5- or 6-membered monocyclic heteroaryl or a polycyclic heteroaryl which is fused with one or more benzene ring(s), and may be partially saturated. The structures having one or more heteroaryl group(s) bonded through a single bond are also included. The heteroaryl groups may include divalent aryl groups of which the heteroatoms are oxidized or quarternized to form N-oxides, quaternary salts, or the like. The term "substituted heteroaryl," as used herein, refers to a heteroaryl in which at least one hydrogen atom is substituted with a substituent composed of an unsubstituted alkyl, a substituted alkyl, at least one heteroatom, and any combination thereof. Heteroatoms include, but are not limited to, O, N, P and S. Substituents include, but are not limited to, halide, OR', NR'$_2$, PR'$_2$, P(=O)R'$_2$, SiR'$_3$; where each R' is independently a $C_1$-$C_{20}$ hydrocarbyl group.

A "heteroatom" is an atom other than carbon or hydrogen. Nonlimiting examples of heteroatoms include: F, Cl, Br, N, O, P, B, S, Si, Sb, Al, Sn, As, Se and Ge.

"Hole injection layer," or "HIL," and like terms, is a layer which transports holes from the anode to the emitting layer. The hole injection layer is typically formed on the anode.

"Hole transport layer (or "HTL")," and like terms, refers to a layer made from a material, which transports holes. High hole mobility is recommended for OLED devices. The HTL is used to help block passage of electrons transported by the emitting layer. Small electron affinity is typically required to block electrons. The HTL should desirably have a higher energy lowest excited state triplet to block exciton migrations from an adjacent EML layer.

The term "hydrocarbon," as used herein, refers to a chemical group containing only hydrogen atoms and carbon atoms. The term "hydrocarbon" includes "a hydrocarbyl" which is a hydrocarbon substituent having a valence (typically univalent). The term "substituted hydrocarbon," (or "substituted hydrocarbyl"), as used herein, refers to a hydrocarbon (or hydrocarbyl) in which at least one hydrogen atom is substituted with a substituent comprising at least one heteroatom. An "unsubstituted hydrocarbon" (or "unsubstituted hydrocarbyl") is a hydrocarbon that contains no heteroatoms.

The term "orbital energies" refers to energy levels of the orbitals of a molecule. Orbitals include HOMO, the highest occupied molecular orbital, LUMO, the lowest occupied molecular orbital. Also of interest is the $S_1$-$T_1$ gap. Orbital energies were calculated for a variety of variations of compound (I). Calculations were performed as follows. The ground-state ($S_0$) and first excited triplet-state ($T_1$) configurations of the molecules were computed using Density Functional Theory (DFT) at B3LYP/6-31g*level. The energies of highest occupied molecular orbital (HOMO) and lowest unoccupied molecular orbital (LUMO) were obtained from the $S_0$ configuration. The energy of the $T_1$ state was computed as the difference in energy between the minima of $S_0$ and $T_1$ potential energy surfaces (PES). The $S_1$-$T_1$ gap was computed as the vertical energy between the $S_1$ and $T_1$ states, at the $T_1$ configuration. The $S_1$-$T_1$ gap was computed using Time Dependent Density Functional Theory (TDDFT). All the calculations were performed using G09 suit of programs (Frisch, M. J.; Trucks, G. W.; Schlegel, H. B.; Scuseria, G. E.; Robb, M. A.; Cheeseman, J. R.; Scalmani, G.; Barone, V.; Mennucci, B.; Petersson, G. A.; Nakatsuji, H.; Caricato, M.; Li, X.; Hratchian, H. P.; Izmaylov, A. F.; Bloino, J.; Zheng, G.; Sonnenberg, J. L.; Hada, M.; Ehara, M.; Toyota, K.; Fukuda, R.; Hasegawa, J.; Ishida, M.; Nakajima, T.; Honda, Y.; Kitao, O.; Nakai, H.; Vreven, T.; Montgomery, J. A., Jr.; Peralta, J. E.; Ogliaro, F.; Bearpark, M.; Heyd, J. J.; Brothers, E.; Kudin, K. N.; Staroverov, V. N.; Kobayashi, R.; Normand, J.; Raghavachari, K.; Rendell, A.; Burant, J. C.; Iyengar, S. S.; Tomasi, J.; Cossi, M.; Rega, N.; Millam, J. M.; Klene, M.; Knox, J. E.; Cross, J. B.; Bakken, V.; Adamo, C.; Jaramillo, J.; Gomperts, R.; Stratmann, R. E.; Yazyev, O.; Austin, A. J.; Cammi, R.; Pomelli, C.; Ochterski, J. W.; Martin, R. L.; Morokuma, K.; Zakrzewski, V. G.; Voth, G. A.; Salvador, P.; Dannenberg, J. J.; Dapprich, S.; Daniels, A. D.; Farkas, Ö.; Foresman, J. B.; Ortiz, J. V.; Cioslowski, J.; Fox, D. J. Gaussian, Inc., Wallingford Conn., 2009). Orbital energies are reported in eV.

The term "organic group" refers to a chemical group that contains one or more carbon atom and also contains one or more atom of an element other than carbon, which may be, for example, hydrogen, halogen, nitrogen, oxygen, sulfur, phosphorous, or another element, or a combination thereof.

A "ring structure," as used herein, is a chemical group that contains three or more atoms covalently bonded to each other in such a way that at least one path can be traced along covalent bonds from a first atom, through two or more other atoms, and back to the first atom. A ring structure may contain carbon, hydrogen, one or more atoms other than carbon and hydrogen, or a combination thereof. A ring structure can be saturated or unsaturated, including aromatic, and the ring structure can contain one, or two, or more than two rings.

A "solvent" is a compound or mixture of compounds that is liquid at 23° C. and that has boiling point (or lowest boiling point, if a mixture) at 1 atmosphere pressure of 30° C. to 150° C. A nonaqueous solvent contains 10% or less water by weight based on the weight of the solvent. A solvent is "aprotic" if the solvent (or every ingredient compound in the solvent, if the solvent is a mixture) is non-acidic and non-basic. A solvent Q is non-acidic if the negative log 10 of the equilibrium constant (pK) of the following reaction is 10 or greater:

A solvent Q is non-basic if the pK of the following reaction is 4 or lower:

A solvent is non-coordinating if it is not effective at forming coordination bonds with transition metal ions.

The "substrate" is a support for the organic light-emitting device. Nonlimiting examples of material suitable for the substrate include quartz plate, glass plate, metal plate, metal foil, plastic film from polymeric resins such as polyester, polymethacrylate, polycarbonate, and polysulfone.

The composition of the present invention contains a compound having structure (I):

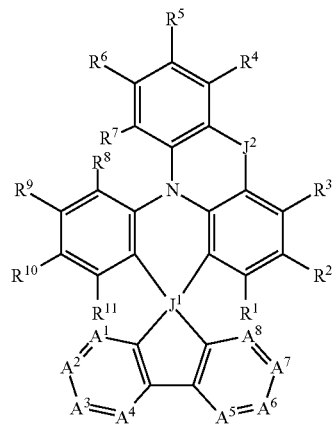

(I)

where each of $A^1$, $A^2$, $A^3$, $A^4$, $A^5$, $A^6$, $A^7$, and $A^8$ is independently $CR^{12}$ or N; where one to four of $A^1$, $A^2$, $A^3$, $A^4$, $A^5$, $A^6$, $A^7$, and $A^8$ is N; where $J^1$ is C or Si; where $J^2$ is $C(R^{13})_n$, O, $(C(R^{13})_n)_2$, S, or Se; where n is 1 or 2; where each of $R^1$, $R^2$, $R^3$, $R^4$, $R^5$, $R^6$, $R^7$, $R^8$, $R^9$, $R^{10}$, $R^{11}$, $R^{12}$, and $R^{13}$ is independently H, deuterium, or an organic group.

Preferably, each of $R^1$, $R^2$, $R^3$, $R^4$, $R^5$, $R^6$, $R^7$, $R^8$, $R^9$, $R^{10}$, $R^{11}$, $R^{12}$, and $R^{13}$ is independently H or an organic group. Each organic group may be polymeric or non-polymeric. Preferably every organic group has 50 or fewer atoms other than hydrogen. Preferably, each of $R^1$, $R^2$, $R^3$, $R^4$, $R^5$, $R^6$, $R^7$, $R^8$, $R^9$, $R^{10}$, $R^1$, $R^{12}$, and $R^{13}$ is independently H or an organic group, where every organic group is selected from substituted aromatic groups, unsubstituted aromatic groups, substituted heteroaromatic groups, and unsubstituted heteroaromatic groups. Preferably, one or more of $R^1$, $R^2$, $R^3$, $R^4$, $R^5$, $R^6$, $R^7$, $R^8$, $R^9$, $R^{10}$, and $R^{11}$, is hydrogen; more preferably two or more; more preferably six or more; more preferably 8 or more; more preferably 10 or more; more preferably, all of $R^1$, $R^2$, $R^3$, $R^4$, $R^5$, $R^6$, $R^7$, $R^8$, $R^9$, $R^{10}$, and $R^1$ are hydrogens.

Preferably, $J^1$ is C.

Preferably, two or more of $A^1$, $A^2$, $A^3$, $A^4$, $A^5$, $A^6$, $A^7$, and $A^8$ is N. Preferably, four or fewer of $A^1$, $A^2$, $A^3$, $A^4$, $A^5$, $A^6$, $A^7$, and $A^8$ is N. More preferably, one or more of $A^1$, $A^2$, $A^3$, and $A^4$ is N and one or more of $A^5$, $A^6$, $A^7$, and $A^8$ is N. More preferably, exactly one of $A^1$, $A^2$, $A^3$, and $A^4$ is N and exactly one of $A^5$, $A^6$, $A^7$, and $A^8$ is N. Preferably, if $A^1$ is N, then $A^8$ is also N. Preferably, if $A^2$ is N, then $A^7$ is also N. Preferably, if $A^3$ is N, then $A^6$ is also N. Preferably, if $A^4$ is N, then $A^5$ is also N.

Preferably, any one of $A^1$, $A^2$, $A^3$, $A^4$, $A^5$, $A^6$, $A^7$, and $A^8$ that is not N is $CR^{12}$, where $R^{12}$ is hydrogen or an organic group selected from substituted aromatic groups, unsubstituted aromatic groups, substituted heteroaromatic groups, and unsubstituted heteroaromatic groups. Preferably, exactly three of $A^1$, $A^2$, $A^3$, and $A^4$ are CH, and exactly three of $A^5$, $A^6$, $A^7$, and $A^8$ are CH. Preferably, one or more of $A^1$, $A^2$, $A^3$, $A^4$, $A^5$, $A^6$, $A^7$, and $A^8$ that is not N is CH; more preferably, every one of $A^1$, $A^2$, $A^3$, $A^4$, $A^5$, $A^6$, $A^7$, and $A^8$ that is not N is CH.

When it is stated herein that $J^2$ is $C(R^{13})$, it is to be understood that

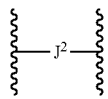

is either

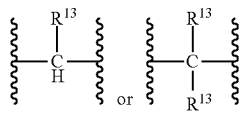

where ⟶ represents a point of attachment to other atoms.

When it is stated herein that $J^2$ is $(C(R^{13})_n)_2$, it is to be understood that

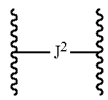

is either

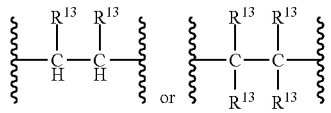

Preferably, $J^2$ is S, Se, O, or $C(R^{13})_n$; more preferably O or $C(R^{13})_n$, where n is 1 or 2 and $R^{13}$ is as defined above. When $J^2$ is $C(R^{13})_n$, preferably, n is 2. When $J^2$ is $C(R^{13})_n$, preferably $R^{13}$ is phenyl or methyl.

In the tables below, for each structure, any R group not explicitly described is hydrogen, and any $A^y$ group not listed is CH. "Ph" is a phenyl group, $C_6H_5$. Some preferred embodiments of structure (I) are as follows.

| Structure Label | $J^1$ | $J^2$ | N atoms |
| --- | --- | --- | --- |
| S1 | C | O | $A^4, A^5$ |
| S2 | C | O | $A^1, A^8$ |
| S3 | C | $C(CH_3)_2$ | $A^1, A^8$ |
| S4 | C | $C(Ph)_2$ | $A^1, A^8$ |
| S5 | C | $C(Ph)_2$ | $A^4, A^5$ |
| S6 | Si | O | $A^1, A^8$ |
| S7 | Si | S | $A^1, A^8$ |

Further preferred structures are as follows:

| Structure Label | $J^1$ | $J^2$ | N atoms |
| --- | --- | --- | --- |
| S8 | Si | $C(CH_3)_2$ | $A^1, A^8$ |
| S9 | Si | $C(Ph)_2$ | $A^1, A^8$ |
| S10 | C | NPh | $A^1, A^8$ |
| S11 | C | Se | $A^1, A^8$ |
| S12 | C | $(CH_2CH_2)$ | $A^1, A^8$ |
| S13 | C | O | $A^2, A^7$ |
| S14 | C | O | $A^6, A^8$ |

Further preferred structures are as follows:

| Structure Label | $J^1$ | $J^2$ | N atoms |
| --- | --- | --- | --- |
| S15 | C | O | $A^5, A^8$ |
| S16 | C | O | $A^1, A^5, A^7$ |
| S17 | C | O | $A^2, A^8$ |
| S18 | C | O | $A^3, A^8$ |
| S19 | C | O | $A^4, A^8$ |
| S20 | C | O | $A^3, A^7$ |
| S21 | C | O | $A^4, A^7$ |

More preferred are S1 through S5 as described above, which have structures as follows:

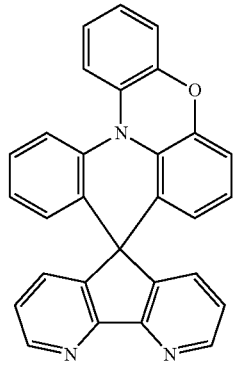

S1

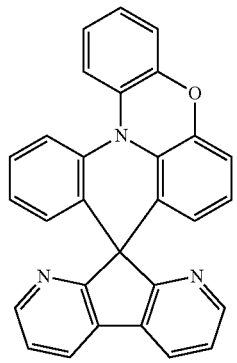

S2

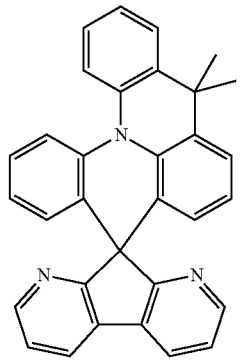

S3

-continued

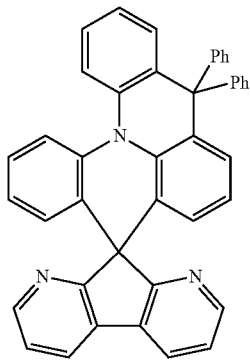
S4

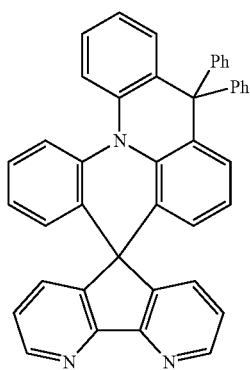
S5

Even more preferred are S1 and S2.

As depicted in structure (I), compound (I) appears to be planar, but it is considered that the molecule of compound (I) contains two planar structures that are effectively perpendicular to each other. The atom at position $J^1$ is known as the "spiro" center. The two bonds extending down in the drawing of structure (I) will form a first plane, and the two bonds extending up in the drawing of structure (I) will form a second plane that is perpendicular to the first plane. The portion of compound (I) below the spiro center is considered to be a planar structure; and this planar structure may be considered to rest in the plane of the drawing of structure (I). The portion of compound (I) above the spiro center is also considered to be planar and is then considered to rest in a plane perpendicular to the plane of the drawing.

One characteristic of compound (I) is the $S_1$-$T_1$ gap. This gap is the energy difference between the lowest excited triplet state $T_1$ and the lowest excited singlet state $S_1$. Preferably, the $S_1$-$T_1$ gap is 0 to 0.6 eV, more preferably 0 to 0.4 eV, more preferably 0 to 0.3 eV.

While the present invention is not limited to any specific mechanism, it is contemplated that the importance of a relatively small $S_1$-$T_1$ gap is as follows. When the $S_1$-$T_1$ gap is small, when the molecule is excited via electrical excitation, an $S_1$ state or a $T_1$ state will form. Using simple spin statistics, typically, approximately 25% of the excited molecules will be in an $S_1$ state, and approximately 75% of the excited molecules will be in a $T_1$ state. The $T_1$ state is lower energy than the $S_1$ state.

In the past, this situation left the OLED designer with a choice. In one choice, molecules with desirable blue-color emission (e.g., blue color) from the $T_1$ state (phosphorescent emitters) had relatively high quantum yield (up to 100%) but were expensive and had short service lifetimes (i.e., devices made from these emitters did not last for a long time in use).

In the other choice, molecules with desirable blue-color emission (e.g., blue color) from the $S_1$ state (fluorescent emitters) had relatively low internal quantum yield, for electrical excitation, (only up to 25%) but were less expensive and had longer lifetimes in service.

It is contemplated that molecules of the present invention, when they have relatively small $S_1$-$T_1$ gap, allow a phenomenon in which excited molecules decay to the $T_1$ state, then thermal energy allows some or all of those molecules to enter the $S_1$ state. In this situation, if (as usual) the fluorescence lifetime of emission from the $S_1$ state is shorter than the phosphorescence lifetime of emission from the $T_1$ state, then the quantum yield can approach 100%. Thus molecules of the present invention may be able to have the advantages of low expense and long service lifetimes characteristic of previously known fluorescent emitters while also having the high internal quantum yield of previously known phosphorescent emitters when used as emitters in electroluminescent devices.

The compound (I) may be made by any method. A preferred method involves providing a compound (II)

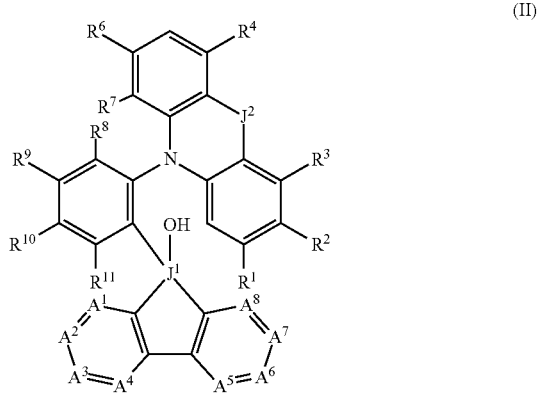
(II)

where $J^1$, $J^2$, $A^1$, $A^2$, $A^3$, $A^4$, $A^5$, $A^6$, $A^7$, $A^8$, $R^1$, $R^2$, $R^3$, $R^4$, $R^5$, $R^6$, $R^7$, $R^8$, $R^9$, $R^{10}$, and $R^{11}$ are defined as in structure (I) above.

The compound (II) may be made by any method. One suitable method of making the compound (II) is as follows:

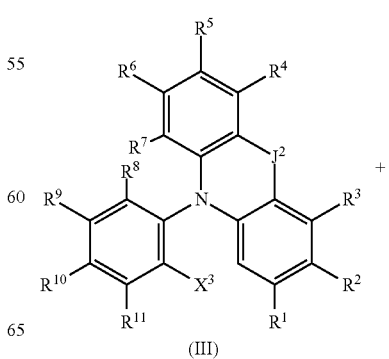
+
(III)

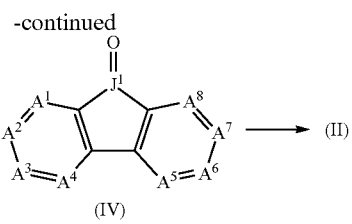

The reaction between (III) and (IV) is preferably carried out in the presence of a strong base (such as, for example butyllithium), and preferably in the presence of a nonaqueous solvent (such as, for example, tetrahydrofuran). In compound (III), $R^1$, $R^2$, $R^3$, $R^4$, $R^5$, $R^6$, $R^7$, $R^8$, $R^9$, $R^{10}$, and $R^{11}$ are defined as in structure (I) above. $X^3$ is a halogen, preferably bromine.

One suitable method of converting compound (II) to compound (I), herein called the "acid method," is a method that includes making a mixture of compound (II) with strong acid, such as, for example, sulfuric acid.

A preferred method (herein called the "base method") of converting compound (II) to compound (I), includes the step of making a mixture (M1) that contains compound (II) and a base having pKa of the conjugate acid of 8 or higher; more preferably 9 or higher. Preferably the base is an organic amine.

Preferably, the mixture (M1) also contains a nonaqueous solvent. Preferably, the amount of water in mixture (M1) is 0 to 5% by weight based on the weight of the mixture (M1); more preferably 0 to 2%; more preferably 0 to 1%. Preferably the nonaqueous solvent is aprotic. Preferably the solvent is non-coordinating. Preferred solvents contain one or more aromatic ring. Preferably the compound (II) and the base are both dissolved in the solvent. Preferably, the mixture (M1) contains a reactant $G_iX$, where G is an organic group and X is either a halogen or is oxygen. When X is a halogen, i is 1; when X is oxygen; i is 2. G is selected from the following (where ⎯⎯} denotes the point of attachment of G to X): methanesulfonyl (mesyl or "Ms"):

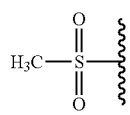

trifluoromethanesulfonyl (triflate or "Tf"):

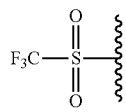

4-methylbenzenesulfonyl (tosyl or "Ts"):

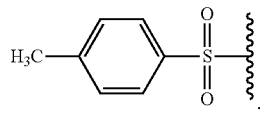

Preferably heat is applied to mixture (M1) to raise the temperature of mixture (M1) from temperature T-LOW to temperature T-HIGH. Preferably, T-Low is 20° C. or lower; more preferably 10° C. or lower; more preferably 2° C. or lower. Preferably, T-High is 50° C. or higher; more preferably 70° C. or higher; more preferably 90° C. or higher; more preferably 105° C. or higher. Preferably T-High is 150° C. or lower. Preferably the step of raising the temperature of mixture (M1) from T-LOW to T-HIGH is performed after compound (II), base, solvent, and reactant $G_iX$ have all been mixed together in mixture (M1).

It is contemplated that the base method proceeds in two successive chemical reactions, as follows:

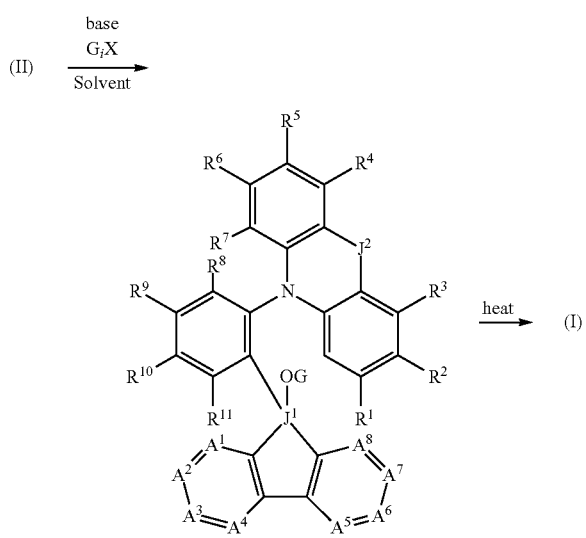

The composition of the present invention may be used for any purpose. A preferred purpose is use as part of an organic light emitting diode (OLED). With reference to FIG. 1, preferably, the composition of the present invention forms all or part of the emitting layer 6 of an OLED. The emitting layer 6 could be made of compound (I). Alternatively, the emitting layer 6 could be made of a host substance in which molecules of a dopant were distributed, and the dopant molecules could include molecules of compound (I). If a host molecule is used, preferably the host molecule has $T_1$ energy higher than that of compound (I). Suitable hosts include, for example, DPEPO, HP012, and organic polymers such as, for example, acrylic polymers, including, for example, poly(methyl methacrylate). DPEPO and HP012 are defined as follows:

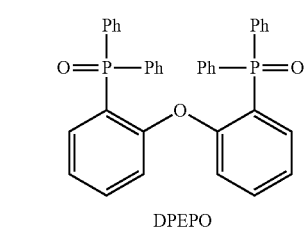

DPEPO

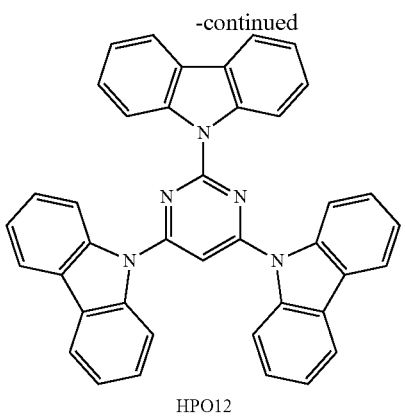

HPO12

Also envisioned are embodiments in which the emitting layer 6 comprises the composition of the present invention acting as a host a dopant. In such embodiments, the dopant could be a phosphorescent dopant in which the orbital energy of the $T_1$ state of the dopant is lower than the orbital energy of the $T_1$ state of the host composition of the present invention.

The material forming the emitting layer 6 could be deposited, for example by vapor thermal evaporation or by solution processing (deposition of a solution followed by evaporation of solvent), on top of a hole transport layer 5.

Also envisioned are embodiments in which the composition of the present invention is present in an optional electron blocking layer (denoted HTL') (not shown in FIG. 1), either alone or as a dopant. An HTL' layer, if present, may be applied by either thermal evaporation or by solution processing.

One embodiment of an OLED is shown in FIG. 1. The anode conductive layer 2 is in contact with HIL1, the first hole injection layer 3, and the other layers are, in order: optional second hole injection layer, HIL2 4; hole transport layer HTL 5, the emitting layer 6, an electron transport layer ETL 7, an electron injection layer 8, and a metal cathode 9. When it is desired that the OLED produce emitted light, a voltage source 10 is connected to the OLED via conductors 11 as shown in FIG. 1. The voltage is preferably applied so that the cathode is at a negative voltage relative to the anode.

The following are examples of the present invention.

Nuclear Magnetic Resonance (NMR) analysis was performed as follows. $^1$H and $^{13}$C NMR spectra were acquired on a Bruker 400 spectrometer, and are referenced to tetramethylsilane. Computational modeling used density functional theory methods B3LYP with the 6-31G* basis set. B3LYP is described in the following references: (a) Becke, A. *The Journal of Chemical Physics* 1993, 98, 5648; (b) Lee, C.; Yang, W.; Parr, R. G. *Physical Review B* 1988, 37, 785; and (c) Miehlich, B.; Savin, A.; Stoll, H.; Preuss, H. *Phys. Lett* 1989, 157, 200. The 6-31G* basis set is described in the following references: (a) Ditchfield, W. *J. Chem. Phys.* 1971, 54, 724; (b) Hehre, W.; Ditchfield, R.; Pople, J. *J. Chem. Phys.* 1972, 56, 2257; and (c) Gordon, M. S. *J. Am. Chem. Soc.* 1980, 102, 7419.

High performance liquid chromatography (HPLC) was performed as follows. Four microliter aliquots of the samples as 2 mg/ml solutions in THF were injected on an Agilent 1200SL binary gradient liquid chromatography coupled to a Agilent 6520 QTof, quadrupole-time of flight MS system via a dual spray electrospray (ESI) interface operating in the positive ion mode. The following analysis conditions were used:

Column: 4.6×150 mm, 3.5 µm Zorbax Exclipse C18
Column temperature: 40° C.
Mobile phase: 45/55 A/B to 20/80 A/B at 32 minutes (hold minutes)
A=0.1 v % formic acid in water
B=THF
Flow: 0.8 mL/min
UV detection: Diode Array 210 to 600 nm
ESI conditions: Gas Temp—365° C. Gas Flow—8 ml/min
Capillary—3.5 kV Nebulizer—40 PSI
Fragmentor—145V
AutoMSMS conditions: Mode—+TOFMS and +TOFMSMS; Centroid Resolution 12000(+)
2 Ghz Extended Mass Range
Scan—50 to 1700 amu (±MS) Rate—3 scan/sec
Scan—50 to 1700 amu (±MS/MS) Rate—3 scan/sec
Collision Energy: −65V Collision Gas: Nitrogen
Isolation width ~9amu
Reference Ions: 121.050873: 922.009798 (+)

The following materials were used:
$Pd_2(dba)_3$ is Tris(dibenzylideneacetone) dipalladium (0).
XPhos ligand is 2-Dicyclohexylphosphino-2',4',6'-triisopropylbiphenyl.
TEA is triethylamine (pKa of the conjugate acid is 10.75)
Ms is the mesyl group, which has the structure $SO_2CH_3$, and which attaches to other atoms via a bond to the sulfur atom of the mesyl group.
Tf is the triflic group, which has the structure $SO_2CF_3$, and which attaches to other atoms via a bond to the sulfur atom of the triflic group.
PhCl is chlorobenzene.
Eaton's Reagent is phosphorous pentoxide, 7.7% by weight in methanesulfonic acid.

In the following examples, room temperature was approximately 23° C.

PREPARATIVE EXAMPLE 1: SYNTHESIS OF COMPOUND (III)

10-(2-bromophenyl)-10H-phenoxazine, which is compound (III), in which $R^1$, $R^2$, $R^3$, $R^4$, $R^5$, $R^6$, $R^7$, $R^8$, $R^9$, $R^{10}$, and $R^{11}$ are all hydrogen; $J^2$ is oxygen; and $X^3$ is bromine, was made as follows.

A 1 L three neck round bottomed flask equipped with an overhead stirrer, a thermocouple, a heat mantle, and a water condenser with a nitrogen inlet was charged with phenoxazine (7.721 g, 42.14 mmol, 1 equiv), sodium tert-butoxide (9.974 g, 10.79 mmol, 2 equiv) and 1,2-iodobromobenzene (6.5 mL, 50.58 mmol, 1.2 equiv). Toluene (400 mL, 0.1 M) that had been sparged with nitrogen for 5 minutes was then added. In a separate flask, a solution of Tris(dibenzylideneacetone)dipalladium(0) (Pd2dba3) (0.769 g, 1.54 mmol, 0.02 equiv) and 2-Dicyclohexylphosphino-2',4',6'-triisopropylbiphenyl (XPhos) (1.219 g, 2.44 mmol, 0.06 equiv) in toluene (20 mL, 0.08 M) was stirred for 30 min at room temperature under nitrogen. The pre-formed catalyst solution was then added to the reaction mixture and the flask was heated to reflux overnight. The reaction was then allowed to cool to room temperature and filtered through a pad of silica gel, washing with dichloromethane. The material was triturated with chloroform to obtain the titled compound as an off white solid (6.1 g, 43% yield, ~96% pure by HPLC). NMR results were as follows:

$^1$H NMR (400 MHz, Chloroform-d) δ 7.83 (dd, J=8.0, 1.5 Hz, 1H), 7.53 (td, J=7.6, 1.5 Hz, 1H), 7.43 (dd, J=7.8, 1.7 Hz, 1H), 7.36 (td, J=7.7, 1.7 Hz, 1H), 6.65 (dddd, J=30.6, 15.0, 7.6, 1.8 Hz, 6H), 5.79 (dd, J=7.8, 1.6 Hz, 2H).

$^{13}$C NMR (101 MHz, CDCl$_3$) δ 143.80, 137.42, 135.04, 133.19, 132.71, 130.28, 130.02, 126.30, 123.32, 121.64, 115.60, 112.91.

PREPARATIVE EXAMPLE 2: SYNTHESIS OF COMPOUND (II)

Synthesis of 5-(2-(10H-phenoxazin-10-yl)phenyl)-5H-cyclopenta[1,2-b:5,4-b']dipyridin-5-ol, which is compound (II) in which R$^1$, R$^2$, R$^3$, R$^4$, R$^5$, R$^6$, R$^7$, R$^8$, R$^9$, R$^{10}$, and R$^{11}$ are all hydrogen, J$^2$ is O, J$^1$ is C, A$^4$ and A$^5$ are N, and A$^1$, A$^2$, A$^3$, A$^6$, A$^7$, and A$^8$ are CH, was performed as follows.

A 100 mL three neck round bottom flask was charged with 10-(2-bromophenyl)-10H-phenoxazine (0.905 g, 2.68 mmol, 1.1 equiv) and anhydrous THF (45 mL) and was cooled to −78° C. 1.6 M n-butyllithium in hexanes (1.67 mL, 2.68 mmol, 1.1 equiv) was added over 5 minutes and the reaction stirred at −78° C. for 1 hour. 4,5-diazafluorenone (0.443 g, 2.43 mmol, 1 equiv) was then added to the lithiated species, forming a purple mixture. After 1 hour at −78° C. the ice bath was removed and the reaction stirred at room temperature for 4 h. The reaction was stopped by the addition of water and extracted with chloroform three times. The combined extracts were dried over magnesium sulfate, filtered and concentrated. The resulting solid was triturated with hexanes to give a light brown solid (0.8 g, 75% yield) that was carried into the next step without further purification.

NMR results were as follows: $^1$H NMR (400 MHz, Chloroform-d) δ 8.62 (dd, J=8.0, 1.5 Hz, 1H), 8.23 (dd, J=4.9, 1.5 Hz, 2H), 7.70 (ddd, J=8.0, 7.4, 1.4 Hz, 1H), 7.62-7.49 (m, 1H), 7.29 (dd, J=7.6, 1.5 Hz, 2H), 7.11 (dd, J=7.7, 1.4 Hz, 1H), 6.69 (dd, J=7.6, 4.9 Hz, 2H), 6.51-6.39 (m, 4H), 6.23 (ddd, J=7.9, 7.0, 1.9 Hz, 2H), 5.20 (dd, J=7.9, 1.4 Hz, 2H).

EXAMPLE 3: SYNTHESIS OF COMPOUND (I), STRUCTURE S1

Synthesis of spiro[cyclopenta[1,2-b:5,4-b']dipyridine-5,9'-quinolino[3,2,1-kl]phenoxazine], which is compound (I) in which R$^1$, R$^2$, R$^3$, R$^4$, R$^5$, R$^6$, R$^7$, R$^8$, R$^9$, R$^{10}$, and R$^{11}$ are all hydrogen, J$^2$ is O, J$^1$ is C, A$^4$ and A$^5$ are N, and A$^1$, A$^2$, A$^3$, A$^6$, A$^7$, and A$^8$ are CH, was performed as follows.

A 100 mL three neck round bottomed flask equipped with a stir bar, thermocouple, heating mantle, and condenser with a nitrogen inlet was charged with tertiary alcohol from Preparative Example 2 (0.730 g, 1.65 mmol, 1 equiv) and acetic acid (40 mL). The red insoluble mixture was heated to 80° C., at which point it became homogeneous and sulfuric acid (0.5 mL) was added. The reaction was heated up to 112° C. for 3 days. The reaction was then allowed to cool to room temperature, poured into 100 mL of water and neutralized with an aqueous solution of sodium hydroxide. The aqueous layer was back extracted with chloroform (×3) and the combined organic layers were dried over magnesium sulfate, filtered and concentrated by rotary evaporation. The crude material was purified via column chromatography on silica gel using dichloromethane: acetone as the solvent system to give the titled compound (30 mg, 4% yield).

NMR results were as follows: $^1$H NMR (400 MHz, Chloroform-d) δ 8.92 (s, 1H), 8.60 (s, 1H), 7.88-7.73 (m, 2H), 7.63 (s, 1H), 7.54-7.42 (m, 2H), 7.26 (s, 2H), 7.15-7.03 (m, 3H), 6.87-6.74 (m, 2H), 6.68 (t, J=8.0 Hz, 1H), 6.59 (dd, J=7.8, 1.5 Hz, 1H), 6.13 (dd, J=7.9, 1.3 Hz, 1H).

PREPARATIVE EXAMPLE 4: SYNTHESIS OF COMPOUND (II)

Synthesis of 9-(2-(10H-phenoxazin-10-yl)phenyl)-9H-cyclopenta[1,2-b:4,3-b']dipyridin-9-ol, which is compound (II) in which R$^1$, R$^2$, R$^3$, R$^4$, R$^5$, R$^6$, R$^7$, R$^1$, R$^9$, R$^{10}$, and R$^{11}$ are all hydrogen, J$^2$ is O, J$^1$ is C, A$^1$ and A$^8$ are N, and A$^2$, A$^3$, A$^4$, A$^5$, A$^6$, and A$^7$ are CH, was performed as follows.

A 250 mL three neck round bottom flask was charged with 10-(2-bromophenyl)-10H-phenoxazine from Preparative Example 1 (4.014 g, 11.87 mmol, 1.1 equiv) and anhydrous THF (150 mL) and was cooled to −78° C. 1.6 M n-butyllithium in hexanes (7.39 mL, 11.83 mmol, 1.1 equiv) was added over 5 minutes and the reaction stirred at −78° C. for 1 hour. 1,8-diazafluorenone (1.870 g, 10.26 mmol, 1 equiv) was then added to the lithiated species forming an orange mixture. After 1 hour at −78° C. the ice bath was removed and the reaction stirred at room temperature for 4 h. The reaction was stopped by the addition of water and extracted with chloroform three times. The combined extracts were dried over magnesium sulfate, filtered and concentrated. The resulting solid was triturated with hexanes to give a light brown solid (3.1 g, 68% yield) that was carried into the next step without further purification.

NMR results were as follows. $^1$H NMR (400 MHz, Chloroform-d) δ 8.66 (dd, J=8.0, 1.6 Hz, 1H), 8.02 (dd, J=5.0, 1.5 Hz, 2H), 7.73-7.66 (m, 1H), 7.63 (dd, J=7.7, 1.5 Hz, 2H), 7.52 (td, J=7.6, 1.5 Hz, 1H), 7.04 (dd, J=7.8, 1.4 Hz, 1H), 6.81 (dd, J=7.7, 5.0 Hz, 2H), 6.46 (td, J=7.6, 1.4 Hz, 2H), 6.38 (dd, J=7.9, 1.5 Hz, 2H), 6.30 (ddd, J=8.0, 7.4, 1.6 Hz, 2H), 5.31 (dd, J=8.0, 1.4 Hz, 2H), 4.14 (s, 1H).

$^{13}$C NMR (101 MHz, CDCl$_3$) δ 164.79, 151.30, 148.44, 143.88, 142.11, 134.37, 133.48, 132.53, 131.89, 130.60, 130.34, 129.99, 128.56, 127.96, 127.74, 123.14, 122.62, 121.02, 114.43, 114.16, 79.78.

EXAMPLE 5: SYNTHESIS OF COMPOUND (I), STRUCTURE S2

Synthesis of Spiro [cyclopenta[1,2-b:4,3-b']dipyridine-9,9'-quinolino[3,2,1-kl]phenoxazine], which is compound (I) in which R$^1$, R$^2$, R$^3$, R$^4$, R$^5$, R$^6$, R$^7$, R$^8$, R$^9$, R$^{10}$, and R$^{11}$ are all hydrogen, J$^2$ is O, J$^1$ is C, A$^1$ and A$^8$ are N, and A$^2$, A$^3$, A$^4$, A$^5$, A$^6$, and A$^7$ are CH, was performed as follows. A 100 mL three neck round bottomed flask equipped with a stir bar, thermocouple, heating mantle, and condenser with a nitrogen inlet was charged with tertiary alcohol (0.508 g, 1.15 mmol, 1 equiv) and trifluoroacetic acid (20 mL) and the green mixture was heated to 70° C. for 30 hours. The reaction was then cooled to room temperature, poured into 100 mL of water and neutralized with an aqueous solution of sodium hydroxide. The aqueous layer was back extracted with chloroform (×3) and the combined organic layers were dried over magnesium sulfate, filtered and concentrated by rotary evaporation. The crude material was purified via column chromatography on silica gel with hexanes: ethyl acetate as the solvent system to give the titled compound (240 mg, 49% yield). Single crystals were grown from dichloromethane: hexanes and analyzed by x-ray diffractometry.

NMR results were as follows. $^1$H NMR (400 MHz, Chloroform-d) δ 8.64 (s, 1H), 8.33 (s, 1H), 8.03 (s, 2H), 7.75 (dd, J=8.3, 1.3 Hz, 1H), 7.72-7.51 (m, 1H), 7.26 (m, 2H), 7.17 (ddd, J=8.5, 7.2, 1.5 Hz, 1H), 7.08-6.89 (m, 3H), 6.82-6.72 (m, 2H), 6.63 (t, J=7.9 Hz, 1H), 6.34 (dd, J=7.9, 1.5 Hz, 1H), 5.91 (dd, J=7.9, 1.3 Hz, 1H).

$^{13}$C NMR (101 MHz, CDCl$_3$) δ 150.12, 148.51, 147.09, 137.66, 131.18, 130.50, 128.17, 127.49, 127.20, 126.99, 125.18, 123.48, 123.43, 123.04, 122.47, 120.54, 117.19, 117.13, 116.08, 114.58, 57.87.

PREPARATIVE EXAMPLE 6: SYNTHESIS OF COMPOUND (III)

Synthesis of 10-(2-bromophenyl)-9,9-dimethyl-9,10-dihydroacridine, which is compound (III) in which R$^1$, R$^2$, R$^3$, R$^4$, R$^5$, R$^6$, R$^7$, R$^8$, R$^9$, R$^{10}$, and R$^{11}$ are all hydrogen, J$^2$ is C(CH$_3$)$_2$, X$^3$ is Br, A$^1$ and A$^8$ are N, and A$^2$, A$^3$, A$^4$, A$^5$, A$^6$, and A$^7$ are CH, was performed as follows.

A 500 mL three neck round bottomed flask equipped with a stir bar, a thermocouple, a heat mantle, and a water condenser with a nitrogen inlet was charged with 9,9-dimethyl-9,10-dihydroacridine (5.751 g, 27.48 mmol, 1 equiv), sodium tert-butoxide (5.261 g, 54.75 mmol, 2 equiv), Pd$_2$(dba)$_3$ (0.507 g, 1.01 mmol, 0.02 equiv) and XPhos ligand (0.784 g, 1.63 mmol, 0.06 equiv) and 1,2-iodobromobenzene (7.0 mL, 54.51 mmol, 2 equiv). Toluene (300 mL, 0.1 M) that had been sparged with nitrogen for 5 minutes was then added and the reaction mixture was heated to reflux overnight. The reaction was then allowed to cool to room temperature and filtered through a pad of silica gel washing with dichloromethane. The material was purified via column chromatography on silica gel using hexanes: dichloromethane to obtain the titled compound as a white solid (3.0 g, 50% yield, ~99.9% pure by HPLC).

NMR results were as follows. $^1$H NMR (400 MHz, Chloroform-d) δ 7.87 (dd, J=8.4, 1.5 Hz, 1H), 7.59-7.51 (m, 1H), 7.50-7.45 (m, 2H), 7.42-7.34 (m, 2H), 7.04-6.89 (m, 4H), 6.11 (dd, J=7.9, 1.5 Hz, 2H), 1.77 (s, 3H), 1.67 (s, 3H).
$^{13}$C NMR (101 MHz, CDCl$_3$) δ 139.73, 139.21, 135.00, 133.54, 129.89, 129.86, 129.76, 126.54, 126.52, 125.69, 120.86, 113.33, 35.96, 33.24, 31.09.

PREPARATIVE EXAMPLE 7: SYNTHESIS OF COMPOUND (II)

Synthesis of 9-(2-(9,9-dimethylacridin-10(9H)-yl)phenyl)-9H-cyclopenta[1,2-b:4,3-b']dipyridin-9-ol, which is compound (II) in which R$^1$, R$^2$, R$^3$, R$^4$, R$^5$, R$^6$, R$^7$, R$^8$, R$^9$, R$^{10}$, and R$^{11}$ are all hydrogen, J$^2$ is C(CH$_3$)$_2$, J$^1$ is C, A$^1$ and A$^8$ are N, and A$^2$, A$^3$, A$^4$, A$^5$, A$^6$, and A$^7$ are CH, was performed as follows. A 250 mL three neck round bottom flask was charged with 10-(2-bromophenyl)-9,9-dimethyl-9,10-dihydroacridine from Preparative Example 6 (2.806 g, 7.70 mmol, 1.1 equiv) and anhydrous THF (80 mL) and was cooled to −78° C. 1.6 M n-butyllithium in hexanes (4.7 mL, 7.70 mmol, 1.1 equiv) was added over 5 minutes and the reaction stirred at −78° C. for 1 hour. 1,8-diazafluorenone (1.258 g, 6.91 mmol, 1 equiv) was then added to the lithiated species forming an orange mixture. After 1 hour at −78° C. the ice bath was removed and the reaction stirred at room temperature for 2 h. The reaction was stopped by the addition of water and extracted with chloroform three times. The combined extracts were dried over magnesium sulfate, filtered and concentrated. The resulting solid was triturated with hexanes to give a light brown solid (2.7 g, 90% yield) that was carried into the next step without further purification.

NMR results were as follows: $^1$H NMR (400 MHz, Chloroform-d) δ 8.72 (dd, J=8.0, 1.6 Hz, 1H), 8.09 (dd, J=5.0, 1.5 Hz, 2H), 7.72 (ddd, J=8.3, 7.4, 1.4 Hz, 1H), 7.53 (td, J=7.5, 1.6 Hz, 1H), 7.41 (dd, J=7.7, 1.5 Hz, 2H), 7.04 (dd, J=7.7, 1.6 Hz, 2H), 6.95 (dd, J=7.8, 1.4 Hz, 1H), 6.78 (dd, J=7.7, 5.0 Hz, 2H), 6.62 (td, J=7.4, 1.4 Hz, 2H), 6.55 (ddd, J=8.7, 7.1, 1.7 Hz, 2H), 5.49 (dd, J=8.3, 1.4 Hz, 2H), 1.54 (s, 3H), 1.50 (s, 3H). $^{13}$C NMR (101 MHz, CDCl$_3$) δ 164.81, 148.86, 141.43, 138.79, 138.46, 132.31, 132.13, 131.38, 129.88, 129.51, 128.77, 127.60, 125.94, 125.41, 122.94, 119.75, 115.80, 79.78, 36.68, 35.54, 34.86.

EXAMPLE 8: SYNTHESIS OF COMPOUND (I), STRUCTURE S3

Synthesis of 9',9'-dimethyl-9'H-spiro[cyclopenta[1,2-b:4,3-b']dipyridine-9,5'-quinolino[3,2,1-de]acridine], which is compound (I) in which R$^1$, R$^2$, R$^3$, R$^4$, R$^5$, R$^6$, R$^7$, R$^8$, R$^9$, R$^{10}$, and R$^{11}$ are all hydrogen, J$^2$ is C(CH$_3$)$_2$, J$^1$ is C, A$^1$ and A$^8$ are N, and A$^2$, A$^3$, A$^4$, A$^5$, A$^6$, and A$^7$ are CH, was performed as follows. A 25 mL three neck round bottomed flask equipped with a stir bar, thermocouple, heating mantle, and condenser with a nitrogen inlet was charged with 9-(2-(9,9-dimethylacridin-10(9H)-yl)phenyl)-9H-cyclopenta[1,2-b:4,3-b']dipyridin-9-ol from Preparative Example 7 (2.7 g, 1.15 mmol, 1 equiv), toluene (120 mL) and trifluoroacetic acid (8.2 mL added in several portions) and the green mixture was heated to 70° C. for 6 days. The reaction was then allowed to cool to room temperature, poured into 100 mL of water and neutralized with an aqueous solution of sodium hydroxide. The aqueous layer was back extracted with chloroform (×3) and the combined organic layers were dried over magnesium sulfate, filtered and concentrated by rotary evaporation. The crude material was purified via column chromatography on silica gel using hexanes: dichloromethane as the solvent system to give the titled compound (2.2 g, 84% yield).

NMR results were as follows. $^1$H NMR (400 MHz, Chloroform-d) δ 8.76 (dd, J=4.9, 1.6 Hz, 1H), 8.17-8.07 (m, 2H), 7.89 (dd, J=7.7, 1.6 Hz, 1H), 7.76 (dd, J=8.1, 1.3 Hz, 1H), 7.63 (dd, J=8.2, 1.2 Hz, 1H), 7.51 (dd, J=7.8, 1.6 Hz, 1H), 7.46 (dd, J=7.8, 4.9 Hz, 1H), 7.33-7.22 (m, 2H), 7.21-7.10 (m, 2H), 7.05 (dd, J=7.7, 4.9 Hz, 1H), 6.90-6.71 (m, 2H), 6.41 (dd, J=7.9, 1.5 Hz, 1H), 6.20 (dd, J=7.8, 1.3 Hz, 1H), 1.92 (s, 3H), 1.31 (s, 3H). $^{13}$C NMR (101 MHz, CDCl$_3$) δ 170.57, 168.31, 150.26, 149.89, 139.84, 139.82, 137.54, 136.84, 135.07, 134.47, 128.67, 128.11, 128.06, 128.04, 127.44, 126.36, 126.04, 123.82, 123.38, 123.13, 122.86, 122.53, 122.50, 122.25, 118.80, 118.10, 58.44, 37.06, 31.27, 22.90.

PREPARATIVE EXAMPLE 9: SYNTHESIS OF COMPOUND (III)

Synthesis of 10-(2-bromophenyl)-9,9-diphenyl-9,10-dihydroacridine, which is compound (III) in which R$^1$, R$^2$, R$^3$, R$^4$, R$^5$, R$^6$, R$^7$, R$^8$, R$^9$, R$^{10}$, and R$^{11}$ are hydrogen, J$^2$ is C(Ph)$_2$, where Ph is a phenyl group, and X$^3$ is Br, was performed as follows. A 1 L three neck round bottomed flask equipped with an overhead stirrer, a thermocouple, a heating mantle, and a water condenser with a nitrogen inlet was charged with 9,9-diphenyl-9,10-dihydroacridine (12.841 g, 38.43 mmol, 1 equiv)., sodium tert-butoxide (7.142 g, 74.32 mmol, 2 equiv) and 1,2-dibromobenzene (9.0 mL, 74.62 mmol, 2 equiv). Toluene (400 mL, 0.1 M) that had been sparged with nitrogen for 5 minutes was then added. In a separate flask, a solution of the Pd$_2$(dba)$_3$ (0.600 g, 1.20 mmol, 0.02 equiv) and the XPhos (1.048 g, 2.24 mmol, 0.06 equiv) in toluene (20 mL, 0.08 M)) was stirred for 30 min at room temperature under nitrogen. The pre-formed catalyst solution was then added to the reaction mixture and the flask was heated to reflux overnight. The reaction was then allowed to cool to room temperature and filtered through a pad of silica gel washing with dichloromethane. The material was purified via column chromatography in silica gel using hexanes: dichloromethane as the solvent system to give the titled compound as an off white solid (10.62 g, 84% yield, ~67% pure by HPLC).

NMR results were as follows. H NMR (400 MHz, Chloroform-d) δ 7.78 (dd, J=8.0, 1.5 Hz, 1H), 7.46 (td, J=7.6, 1.5 Hz, 1H), 7.33 (td, J=7.7, 1.7 Hz, 1H), 7.29-7.16 (m, 6H), 7.13 (dd, J=7.8, 1.7 Hz, 1H), 7.09-6.97 (m, 6H), 6.96-6.85 (m, 4H), 6.28 (d, J=7.9 Hz, 2H). $^{13}$C NMR (101 MHz, CDCl$_3$) δ 146.09, 139.82, 130.35, 130.31, 128.03, 127.65, 127.21, 126.32, 120.32, 113.63, 56.79.

PREPARATIVE EXAMPLE 10: SYNTHESIS OF COMPOUND (II)

5-(2-(9,9-diphenylacridin-10(9H)-yl)phenyl)-5H-cyclopenta[1,2-b:5,4-b']dipyridin-5-ol, which is compound (II) in which $R^1$, $R^2$, $R^3$, $R^4$, $R^5$, $R^6$, $R^7$, $R^8$, $R^9$, $R^{10}$, and $R^1$ are hydrogen, $J^2$ is C(Ph)$_2$, where Ph is a phenyl group, $J^1$ is C, $A^4$ and $A^5$ are N, and $A^1$, $A^2$, $A^3$, $A^6$, $A^7$, and $A^8$ are CH, was performed as follows. A 100 mL three neck round bottom flask was charged with 10-(2-bromophenyl)-9,9-diphenyl-9,10-dihydroacridine from Preparative Example 9 (5.3 g, 10.85 mmol, 1.1 equiv) and anhydrous THF (100 mL) and was cooled to −78° C. 1.6M n-butyllithium in hexanes (6.8 mL, 10.85 mmol, 1.1 equiv) was added over 5 minutes and the reaction stirred at −78° C. for 1 hour. 4,5-diazafluorenone (1.80 g, 9.86 mmol, 1 equiv) was then added to the lithiated species forming a purple mixture. After 1 hour at −78° C. the ice bath was removed and the reaction stirred at room temperature for 3 hours. The reaction was stopped by the addition of water and extracted with chloroform three times. The combined extracts were dried over magnesium sulfate, filtered and concentrated. The resulting solid was triturated with hexanes to give a light brown solid (4.0 g, 70% yield) that was carried into the next step without further purification.

NMR results were as follows. $^1$H NMR (400 MHz, Chloroform-d) δ 8.58 (dd, J=4.9, 1.5 Hz, 2H), 7.49 (ddd, J=8.4, 7.2, 1.5 Hz, 1H), 7.41-7.29 (m, 4H), 7.28-7.14 (m, 6H), 7.14-6.95 (m, 9H), 6.94-6.87 (m, 1H), 6.83 (dd, J=8.4, 1.3 Hz, 2H), 6.78 (dd, J=8.2, 1.5 Hz, 1H), 6.48 (dd, J=8.2, 1.2 Hz, 2H). $^{13}$C NMR (101 MHz, CDCl$_3$) δ 157.34, 150.90, 146.30, 144.96, 144.64, 143.74, 141.74, 140.84, 134.41, 132.18, 131.46, 130.53, 130.34, 130.13, 129.64, 129.17, 128.52, 128.32, 127.74, 127.07, 127.01, 126.82, 123.45, 121.61, 116.07, 81.78, 56.84.

EXAMPLE 11: SYNTHESIS OF COMPOUND (I), STRUCTURE S5

Synthesis of 9',9'-diphenyl-9'H-spiro[cyclopenta[1,2-b:5,4-b']dipyridine-5,5'-quinolino[3,2,1-de]acridine], which is compound (I) in which $R^1$, $R^2$, $R^3$, $R^4$, $R^5$, $R^6$, $R^7$, $R^8$, $R^9$, $R^{10}$, and $R^{11}$ are hydrogen, $J^2$ is C(Ph)$_2$, where Ph is a phenyl group, $J^1$ is C, $A^4$ and $A^5$ are N, and $A^1$, $A^2$, $A^3$, $A^6$, $A^7$, and $A^8$ are CH, was performed as follows. A 250 mL round bottomed flask was equipped with a stir bar, a thermocouple and a water condenser with a nitrogen inlet and charged with 5-(2-(9,9-diphenylacridin-10(9H)-yl)phenyl)-5H-cyclopenta[1,2-b:5,4-b']dipyridin-5-ol from Preparative Example 10 (0.5 g, 0.85 mmol, 1 equiv) and the chlorobenzene (60 mL, 0.01 M). The mixture was heated until it became homogeneous (to about 50° C.) and then triethylamine (1.8 mL, 12.7 mmol, 15 equiv) was added. The reaction was then cooled down to 0° C. using an ice bath and methanesulfonic chloride (0.8 mL, 10.1 mmol, 12 equiv) was slowly added. The reaction was stirred for 15 min at 0° C., allowed to warm to room temperature and finally warmed to 115° C. After 3 hours the reaction was quenched by the addition of water and extracted with chloroform (×3). The organic fractions were combined, dried over magnesium sulfate, filtered and concentrated via rotary evaporation. The crude product was then purified via column chromatography in a NH-bound silica column using hexanes: ethyl acetate as the solvent system to give the name product as a white solid (0.25 g, 52% yield).

NMR results were as follows. $^1$H NMR (400 MHz, Chloroform-d) δ 8.92 (dd, J=4.8, 1.5 Hz, 1H), 8.59 (dd, J=4.9, 1.5 Hz, 1H), 7.82 (dd, J=7.7, 1.5 Hz, 1H), 7.68 (dd, J=8.1, 1.3 Hz, 1H), 7.51 (dd, J=7.8, 1.5 Hz, 1H), 7.44 (dd, J=7.7, 4.8 Hz, 1H), 7.41-7.35 (m, 1H), 7.35-7.29 (m, 3H), 7.26 (m, 4H), 7.21-7.10 (m, 4H), 7.06 (ddd, J=8.3, 7.2, 1.5 Hz, 1H), 6.99 (dd, J=7.8, 4.8 Hz, 1H), 6.95 (dd, J=7.9, 1.5 Hz, 1H), 6.90 (dd, J=7.6, 1.5 Hz, 2H), 6.84-6.78 (m, 1H), 6.78-6.71 (m, 1H), 6.53 (dd, J=7.9, 1.5 Hz, 1H), 6.45 (dd, J=7.8, 1.4 Hz, 1H).

PREPARATIVE EXAMPLE 12: SYNTHESIS OF COMPOUND (II)

Synthesis of 9-(2-(9,9-dimethylacridin-10(9H)-yl)phenyl)-9H-cyclopenta[1,2-b:4,3-b']dipyridin-9-ol, which is compound (II) in which $R^1$, $R^2$, $R^3$, $R^4$, $R^5$, $R^6$, $R^7$, $R^8$, $R^9$, $R^{10}$, and $R^{11}$ are hydrogen, $J^2$ is C(Ph)$_2$, where Ph is a phenyl group, $J^1$ is C, $A^1$ and $A^8$ are N, and $A^2$, $A^3$, $A^4$, $A^5$, $A^6$, and $A^7$ are CH, was performed as follows. A 250 mL three neck round bottom flask was charged with 10-(2-bromophenyl)-9,9-dimethyl-9,10-dihydroacridine from Preparative Example 9 (2.806 g, 7.70 mmol, 1.1 equiv) and anhydrous THF (80 mL) and was cooled to −78° C. 1.6M n-butyllithium in hexanes (4.7 mL, 7.70 mmol, 1.1 equiv) was added over 5 minutes and the reaction stirred at −78° C. for 1 hour. 1,8-diazafluorenone (1.258 g, 6.91 mmol, 1 equiv) was then added to the lithiated species forming an orange mixture. After 1 hour at −78° C. the ice bath was removed and the reaction stirred at room temperature for 2 h. The reaction was stopped by the addition of water and extracted with chloroform three times. The combined extracts were dried over magnesium sulfate, filtered and concentrated. The resulting solid was triturated with hexanes to give a light brown solid (2.7 g, 90% yield) that was carried into the next step without further purification.

NMR results were as follows. $^1$H NMR (400 MHz, Chloroform-d) δ 8.72 (dd, J=8.0, 1.6 Hz, 1H), 8.09 (dd, J=5.0, 1.5 Hz, 2H), 7.72 (ddd, J=8.3, 7.4, 1.4 Hz, 1H), 7.53 (td, J=7.5, 1.6 Hz, 1H), 7.41 (dd, J=7.7, 1.5 Hz, 2H), 7.04 (dd, J=7.7, 1.6 Hz, 2H), 6.95 (dd, J=7.8, 1.4 Hz, 1H), 6.78 (dd, J=7.7, 5.0 Hz, 2H), 6.62 (td, J=7.4, 1.4 Hz, 2H), 6.55 (ddd, J=8.7, 7.1, 1.7 Hz, 2H), 5.49 (dd, J=8.3, 1.4 Hz, 2H), 1.54 (s, 3H), 1.50 (s, 3H). $^{13}$C NMR (101 MHz, CDCl$_3$) δ 164.81, 148.86, 141.43, 138.79, 138.46, 132.31, 132.13, 131.38, 129.88, 129.51, 128.77, 127.60, 125.94, 125.41, 122.94, 119.75, 115.80, 79.78, 36.68, 35.54, 34.86.

EXAMPLE 13: SYNTHESIS OF COMPOUND (I), STRUCTURE S4

Synthesis of 9',9'-dimethyl-9'H-spiro[cyclopenta[1,2-b:4,3-b']dipyridine-9,5'-quinolino[3,2,1-de]acridine], which is compound (I) in which $R^1$, $R^2$, $R^3$, $R^4$, $R^5$, $R^6$, $R^7$, $R^8$, $R^9$, $R^{10}$, and $R^{11}$ are hydrogen, $J^2$ is C(Ph)$_2$, where Ph is a phenyl group, $J^1$ is C, $A^1$ and $A^8$ are N, and $A^2$, $A^3$, $A^4$, $A^5$, $A^6$, and $A^7$ are CH, was performed as follows. A 25 mL three neck round bottomed flask equipped with a stir bar, thermocouple, heating mantle, and condenser with a nitrogen inlet was charged with 9-(2-(9,9-dimethylacridin-10(9H)-yl)phenyl)-9H-cyclopenta[1,2-b:4,3-b']dipyridin-9-ol (2.7 g, 1.15 mmol, 1 equiv), toluene (120 mL) and trifluoroacetic acid (8.2 mL added in several portions) and the green mixture was heated to 70° C. for 6 days. The reaction was then allowed to cool to room temperature, poured into 100 mL of water and neutralized with an aqueous solution of sodium hydroxide. The aqueous layer was back extracted with chloroform (×3) and the combined organic layers were dried over magnesium sulfate, filtered and concentrated by rotary evaporation. The crude material was purified via column chromatography on silica gel using hexanes: dichloromethane as the solvent system to give the titled compound (2.2 g, 84% yield).

NMR results were as follows. $^1$H NMR (400 MHz, Chloroform-d) δ 8.76 (dd, J=4.9, 1.6 Hz, 1H), 8.17-8.07 (m, 2H), 7.89 (dd, J=7.7, 1.6 Hz, 1H), 7.76 (dd, J=8.1, 1.3 Hz, 1H), 7.63 (dd, J=8.2, 1.2 Hz, 1H), 7.51 (dd, J=7.8, 1.6 Hz, 1H), 7.46 (dd, J=7.8, 4.9 Hz, 1H), 7.33-7.22 (m, 2H), 7.21-7.10 (m, 2H), 7.05 (dd, J=7.7, 4.9 Hz, 1H), 6.90-6.71 (m, 2H), 6.41 (dd, J=7.9, 1.5 Hz, 1H), 6.20 (dd, J=7.8, 1.3 Hz, 1H), 1.92 (s, 3H), 1.31 (s, 3H). $^{13}$C NMR (101 MHz, CDCl$_3$) δ 170.57, 168.31, 150.26, 149.89, 139.84, 139.82, 137.54, 136.84, 135.07, 134.47, 128.67, 128.11, 128.06, 128.04, 127.44, 126.36, 126.04, 123.82, 123.38, 123.13, 122.86, 122.53, 122.50, 122.25, 118.80, 118.10, 58.44, 37.06, 31.27, 22.90.

EXAMPLES 14: PREFERRED SYNTHESIS METHOD FOR COMPOUND (I), STRUCTURE S5

Three samples of S5 were made using three variations of the preferred synthesis method. All three variations followed the following reaction scheme:

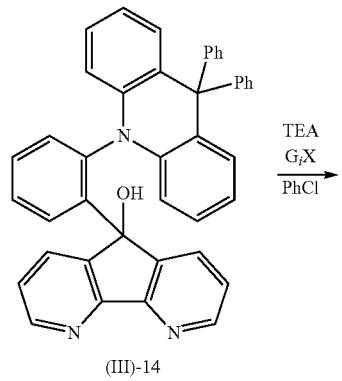

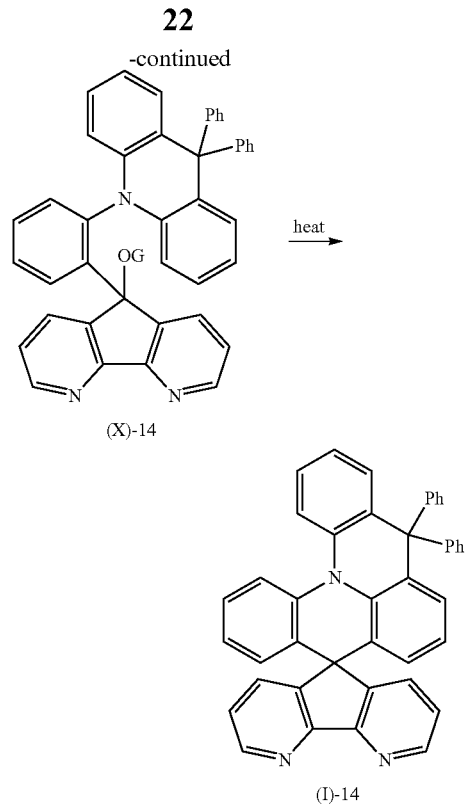

EXAMPLE 14A: G$_j$X=MSCL

A 250 mL round bottomed flask was equipped with a stir bar, a thermocouple and a water condenser with a nitrogen inlet and charged with 5-(2-(9,9-diphenylacridin-10(9H)-yl)phenyl)-5H-cyclopenta[1,2-b:5,4-b']dipyridin-5-ol (0.5 g, 0.85 mmol, 1 equiv) and the chlorobenzene (60 mL, 0.01 M). The mixture was heated until it became homogeneous (to about 50° C.) and then triethylamine (1.8 mL, 12.7 mmol, 15 equiv) was added. The reaction was then cooled down to 0° C. using an ice bath and methanesulfonic chloride (0.8 mL, 10.1 mmol, 12 equiv) was slowly added. The reaction was stirred for 15 min at 0° C., allowed to warm to room temperature and finally warmed to 115° C. After 3 hours the reaction was quenched by the addition of water and extracted with chloroform (×3). The organic fractions were combined, dried over magnesium sulfate, filtered and concentrated via rotary evaporation. The crude product was then purified via column chromatography in a NH-bound silica column using hexanes: ethyl acetate as the solvent system to give the name product as a white solid (0.25 g, 52% yield).

NMR results were as follows: $^1$H NMR (400 MHz, Chloroform-d) δ 8.92 (dd, J=4.8, 1.5 Hz, 1H), 8.59 (dd, J=4.9, 1.5 Hz, 1H), 7.82 (dd, J=7.7, 1.5 Hz, 1H), 7.68 (dd, J=8.1, 1.3 Hz, 1H), 7.51 (dd, J=7.8, 1.5 Hz, 1H), 7.44 (dd, J=7.7, 4.8 Hz, 1H), 7.41-7.35 (m, 1H), 7.35-7.29 (m, 3H), 7.26 (m, 4H), 7.21-7.10 (m, 4H), 7.06 (ddd, J=8.3, 7.2, 1.5 Hz, 1H), 6.99 (dd, J=7.8, 4.8 Hz, 1H), 6.95 (dd, J=7.9, 1.5 Hz, 1H), 6.90 (dd, J=7.6, 1.5 Hz, 2H), 6.84-6.78 (m, 1H), 6.78-6.71 (m, 1H), 6.53 (dd, J=7.9, 1.5 Hz, 1H), 6.45 (dd, J=7.8, 1.4 Hz, 1H).

EXAMPLE 14B: G$_j$X=TF-O-TF

A 250 mL round bottomed flask was equipped with a stir bar, a thermocouple and a water condenser with a nitrogen inlet and charged with 5-(2-(9,9-diphenylacridin-10(9H)-yl)phenyl)-5H-cyclopenta[1,2-b:5,4-b']dipyridin-5-ol (0.5 g, 0.85 mmol, 1 equiv) and the chlorobenzene (60 mL, 0.01 M). The mixture was heated until it became homogeneous (to about 50° C.) and then triethylamine (0.18 mL, 1.27 mmol, 1.5 equiv) was added. The reaction was then cooled down to 0° C. using an ice bath and triflic anhydride (0.18 mL, 1.01 mmol, 1.2 equiv) was slowly added. The reaction was stirred for 15 min at 0° C., allowed to warm to room temperature and finally warmed to 115° C. After 72 hours the reaction was analyzed by HPLC and 60% conversion to the desired product was observed.

EXAMPLE 14C: $G_iX$=MS-O-MS

A 250 mL round bottomed flask was equipped with a stir bar, a thermocouple and a water condenser with a nitrogen inlet and charged with 5-(2-(9,9-diphenylacridin-10(9H)-yl)phenyl)-5H-cyclopenta[1,2-b:5,4-b']dipyridin-5-ol (0.5 g, 0.85 mmol, 1 equiv) and the chlorobenzene (60 mL, 0.01 M). The mixture was heated until it became homogeneous (to about 50° C.) and then triethylamine (1.24 mL, 8.73 mmol, 10.3 equiv) was added. The reaction was then cooled down to 0° C. using an ice bath and methanesulfonic anhydride (0.68 g, 3.9 mmol, 4.6 equiv) was slowly added. The reaction was stirred for 15 min at 0° C., allowed to warm to room temperature and finally warmed to 50° C. After 3 hours the reaction was quenched by the addition of water and extracted with dichloromethane (×3). The organic fractions were combined, dried over magnesium sulfate, filtered and concentrated via rotary evaporation to obtain 0.2 g of the desired product (42% yield).

COMPARATIVE EXAMPLES 15-COMP: ATTEMPTED SYNTHESES BY ACID METHODS

Two attempts were made to convert compound (II)-14 to compound (I)-14 (structures as defined in Example 14 above) using an acid method.

COMPARATIVE EXAMPLE 15A-COMP: EATON'S REAGENT

A 100 mL three neck round bottomed flask equipped with a stir bar, thermocouple, heat mantle, and water condenser with nitrogen inlet and was charged with alcohol (600 mg, 1.01 mmol)—and Eaton's reagent (5 mL). The mixture was heated to 60° C. for 3 days. The reaction was then allowed to cool to room temperature, poured into 100 mL of water and neutralized with an aqueous solution of sodium hydroxide. A black insoluble solid got suspended in the mixture. Product was not detected by HPLC or NMR spectroscopy.

COMPARATIVE EXAMPLE 15B-COMP: SULFURIC ACID

A 100 mL three neck round bottomed flask equipped with a stir bar, thermocouple, heating mantle, and condenser with a nitrogen inlet was charged with tertiary alcohol (1 g, 1.68 mmol, 1 equiv) and acetic acid (40 mL). The red insoluble mixture was heated to 80° C., at which point it became homogeneous and sulfuric acid (0.5 mL) was added. The reaction was heated up to 112° C. for 3 days. The reaction was then allowed to cool to room temperature, poured into 100 mL of water and neutralized with an aqueous solution of sodium hydroxide. The aqueous layer was back extracted with chloroform (×3) and the combined organic layers were dried over magnesium sulfate, filtered and concentrated by rotary evaporation. Only trace amounts (<1 wt %) of desired product were collected.

EXAMPLE 16: PREFERRED METHOD OF SYNTHESIS OF COMPOUND (I), STRUCTURE S1

Using the method of Example 14, where the starting material was structure (II) in which $R^1$, $R^2$, $R^3$, $R^4$, $R^5$, $R^6$, $R^7$, $R^8$, $R^9$, $R^{10}$, and $R^{11}$ were hydrogen, $J^2$ was 0, $J^1$ was C, $A^4$ and $A^5$ were N, and $A^1$, $A^2$, $A^3$, $A^6$, $A^7$, and $A^8$ were CH, structure $S_1$ was made. $G_iX$ was Ms-O-Ms. The mixture was heated at 50° C. for 3 hours. Yield was 70%.

EXAMPLE 17: PREFERRED METHOD OF SYNTHESIS OF COMPOUND (I), STRUCTURE S4

Using the method of Example 14, where the starting material was structure (II) in which $R^1$, $R^2$, $R^3$, $R^4$, $R^5$, $R^6$, $R^7$, $R^8$, $R^9$, $R^{10}$, and $R^{11}$ are hydrogen, $J^2$ is $C(Ph)_2$, where Ph is phenyl, $J^1$ is C, $A^1$ and $A^8$ are N, and $A^2$, $A^3$, $A^4$, $A^5$, $A^6$, and $A^7$ are CH, structure S4 was made. $G_iX$ was Ms-O-Ms. The mixture was heated at 50° C. for 2 hours. Yield was 91%.

The preferred base method of synthesizing compound (I), as demonstrated in Examples 14a, 14b, 14c, 16, and 17, gave superior yield at relatively short reaction times when compared to all of the other examples of synthesizing compound (I), which all used an acid method.

EXAMPLE 18: CALCULATED ORBITAL ENERGY CALCULATIONS, REPORTED IN EV

| Label | HOMO | LUMO | $T_1$ | $S_1$-$T_1$ gap |
| --- | --- | --- | --- | --- |
| S1 | −5.03 | −1.42 | 2.95 | 0.59 |
| S2 | −4.64 | −1.48 | 3.14 | 0.18 |
| S3 | −4.79 | −1.43 | 3.10 | 0.10 |
| S4 | −4.82 | −1.45 | 3.10 | 0.10 |
| S5 | −5.19 | −1.37 | 2.95 | 0.61 |
| S6 | −4.87 | −1.48 | 2.82 | 0.32 |
| S7 | −5.05 | −1.52 | 2.82 | 0.50 |
| S8 | −5.02 | −1.416 | 2.82 | 0.55 |
| S9 | −5.03 | −1.43 | 2.82 | 0.55 |
| S10 | −4.23 | −1.38 | 2.60 | 0.01 |

Additional orbital energy calculation results were as follows:

| Label | HOMO | LUMO | T1 | $S_1$-$T_1$ gap |
| --- | --- | --- | --- | --- |
| S11 | −4.87 | −1.53 | 2.88 | 0.24 |
| S12 | −4.90 | −1.45 | 2.88 | 0.37 |
| S13 | −5.00 | −1.72 | 2.91 | −.026 |
| S14 | −4.92 | −1.40 | 2.87 | 0.27 |
| S15 | −4.80 | −1.62 | 2.79 | 0.05 |
| S16 | −4.98 | −1.84 | 2.91 | 0.01 |
| S17 | −4.78 | −1.60 | 2.90 | 0.01 |
| S18 | −4.82 | −1.40 | 2.92 | 0.39 |
| S19 | −4.78 | −1.45 | 2.89 | 0.12 |
| S20 | −5.03 | −1.52 | 2.93 | 0.54 |
| S21 | −4.99 | −1.56 | 2.93 | 0.45 |

EXAMPLE 19: PHOTOLUMINESCENCE RESULTS

Films were made at 100 nm thickness, 10% compound (I) by weight, in host of DPEPO (defined above), and excited by light at 350 nm. Reported are photoluminescence quantum yield (PLQY) (%); Absorption (Abs) (%); wavelength of maximum fluorescence emission ($\Delta_{max}$); and the full width of the photoluminescence spectrum at half maximum (FWHM).

| Sample | PLQY (%) | Abs (%) | $\lambda_{max}$, nm | FWHM (nm) |
|---|---|---|---|---|
| S1 | 36.9 | 13.4 | 475 | 90 |
| S2 | 45.5 | 13.9 | 470 | 120 |

Both S1 and S2 show desirably high PLQY and Absorption. Both emit blue light as desired, and both have desirably narrow FWHM.

The invention claimed is:

1. A composition comprising a compound having structure (I)

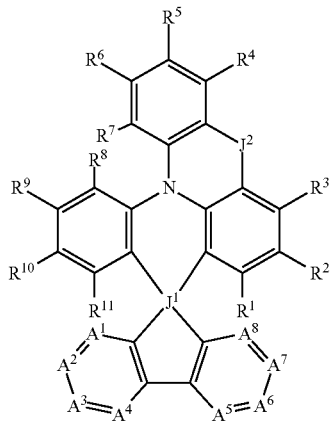

(I)

wherein each of $A^1$, $A^2$, $A^3$, $A^6$, $A^7$, and $A^8$ is independently $CR^{12}$; wherein each of $A^4$ and $A^5$ is independently N; wherein $J^1$ is C; wherein $J^2$ is O; wherein each of $R^1$, $R^2$, $R^3$, $R^4$, $R^5$, $R^6$, $R^7$, $R^8$, $R^9$, $R^{10}$, $R^{11}$, and $R^{12}$ is independently H.

2. A method of making the composition of claim 1, comprising making a mixture of a compound having structure II, a base having pKa of the conjugate acid of 8 or higher, and a compound $G_iX$, wherein structure II is

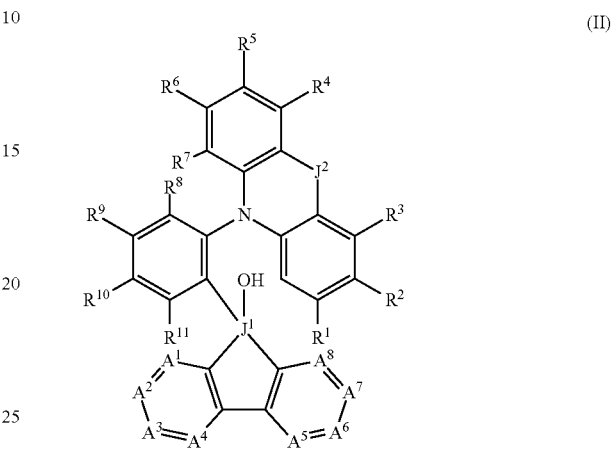

(II)

wherein G is selected from the group consisting of methanesulfonyl, trifluoromethanesulfonyl, and 4-methylbenzenesulfonyl; wherein X is a halogen or O; with the proviso that if X is a halogen, then i is 1, and if X is O, then i is 2.

3. The method of claim 2, wherein the mixture additionally comprises a nonaqueous solvent.

4. The method of claim 2, wherein the method additionally comprises the step of heating the mixture from a temperature of 20° C. or lower to a temperature of 50° C. or higher.

5. A method of making an organic light-emitting diode comprising the step of forming a layer on a substrate, wherein the layer comprises the composition of claim 1.

6. An organic light-emitting diode comprising the composition of claim 1.

* * * * *